(12) United States Patent
Corbucci (10) Patent No.: US 8,041,424 B2
(45) Date of Patent: Oct. 18, 2011

(54) CARDIAC RESYNCHRONIZATION THERAPY FOR PATIENTS WITH RIGHT BUNDLE BRANCH BLOCK

(75) Inventor: Giorgio Corbucci, Cento (IT)

(73) Assignee: Medtronic, Inc., Minneapolis, MN (US)

( * ) Notice: Subject to any disclaimer, the term of this patent is extended or adjusted under 35 U.S.C. 154(b) by 618 days.

(21) Appl. No.: 11/831,403

(22) Filed: Jul. 31, 2007

(65) Prior Publication Data

US 2009/0036941 A1    Feb. 5, 2009

(51) Int. Cl.
*A61N 1/362* (2006.01)

(52) U.S. Cl. .......................................... 607/9

(58) Field of Classification Search .......... 600/508–514, 600/29, 547.119; 607/4, 9, 14–19, 24–25
See application file for complete search history.

(56) References Cited

U.S. PATENT DOCUMENTS

| | | | |
|---|---|---|---|
| 5,330,511 A | 7/1994 | Boute | |
| 5,368,040 A | 11/1994 | Carney | |
| 5,554,177 A | 9/1996 | Kieval et al. | |
| 5,700,283 A | 12/1997 | Salo et al. | |
| 5,814,077 A | 9/1998 | Sholder et al. | |
| 5,836,987 A * | 11/1998 | Baumann et al. | 607/17 |
| 6,029,087 A | 2/2000 | Wohlgemuth | |
| 6,480,733 B1 | 11/2002 | Turcott et al. | |
| 6,643,548 B1 * | 11/2003 | Mai et al. | 607/17 |
| 6,665,564 B2 * | 12/2003 | Lincoln et al. | 607/17 |
| 6,792,308 B2 * | 9/2004 | Corbucci | 607/17 |
| 6,869,404 B2 | 3/2005 | Schulhauser et al. | |
| 6,882,882 B2 | 4/2005 | Struble et al. | |
| 7,526,338 B1 * | 4/2009 | Gill et al. | 607/18 |
| 7,546,161 B1 * | 6/2009 | Bjorling et al. | 607/28 |
| 2004/0215249 A1 | 10/2004 | Corbucci | |
| 2004/0230229 A1 | 11/2004 | Lovett et al. | |
| 2006/0020294 A1 | 1/2006 | Brockway et al. | |
| 2006/0047320 A1 | 3/2006 | Ding et al. | |
| 2006/0178589 A1 * | 8/2006 | Dobak, III | 600/514 |
| 2006/0247548 A1 * | 11/2006 | Sarkar et al. | 600/515 |
| 2007/0043398 A1 | 2/2007 | Ternes et al. | |

OTHER PUBLICATIONS

Textbook of Cardiovascular Medicine; Lippincott Williams and Wilkins, 2007. ISBN 10-7817-702-2, p. 983.*
Brignole, M. et al., "Guidelines on management (diagnosis and treatment) of syncope" European Heart Journal, 2001; pp. 1256-1306; vol. 22.
Hesse, B. et al. "Complete bundle branch block as an independent predictor of all-cause mortality: Report of 7,073 patients referred for nuclear exercise testing", Am. J. Med. 2001; pp. 253-259, vol. 110.
Solomon et al., "Cardiac Resynchronization Therapy Decreases the Number of Third and Fourth Heart Sounds", Heart Rhythm, vol. 2, No. 5, May 1, 2005 Supplement, p. S286.
International Search Report, PCT Application PCT/US2008/070437.

* cited by examiner

Primary Examiner — Carl H Layno
Assistant Examiner — Paula J Stice
(74) Attorney, Agent, or Firm — Stephen W. Bauer; Reed A. Duthler (57) ABSTRACT

An implantable medical device and associated method deliver cardiac resynchronization therapy in a patient having right bundle branch block by measuring an interval between a right atrial depolarization and a first heart sound and selecting a right atrial-ventricular (AV) pacing interval in response to the measured interval. Pacing pulses are delivered to the right ventricle of a patient's heart at the selected right AV pacing interval to synchronize the right ventricle with an intrinsic left ventricle depolarization.

12 Claims, 9 Drawing Sheets

CARDIAC RESYNCHRONIZATION THERAPY FOR PATIENTS WITH RIGHT BUNDLE BRANCH BLOCK

CROSS-REFERENCE TO RELATED APPLICATIONS

U.S. Pat. Application Publication No. 2004/0215249, entitled "Cardiac Resynchronization via left ventricular pacing", flied on Apr. 23, 2003, is hereby incorporated herein by reference in its entirety.

TECHNICAL FIELD

The invention relates generally to implantable medical devices and, in particular, to a device and method for controlling cardiac resynchronization therapy (CRT).

BACKGROUND

CRT is a cardiac electrical stimulation therapy that can benefit patients suffering from heart failure by resynchronizing heart chamber contractions. In particular, patients can benefit from synchronization of the right and left ventricles by delivering pacing pulses in one or both chambers. Patients having right bundle branch block (RBBB) have normal left ventricular electrical activation with an impaired right ventricular electrical depolarization resulting in a wider QRS signal and ventricular dysynchrony. As such, patients having RBBB, with or without heart failure symptoms, may benefit from CRT by restoring the synchronization of the right and left ventricles.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements.

Figure 1:
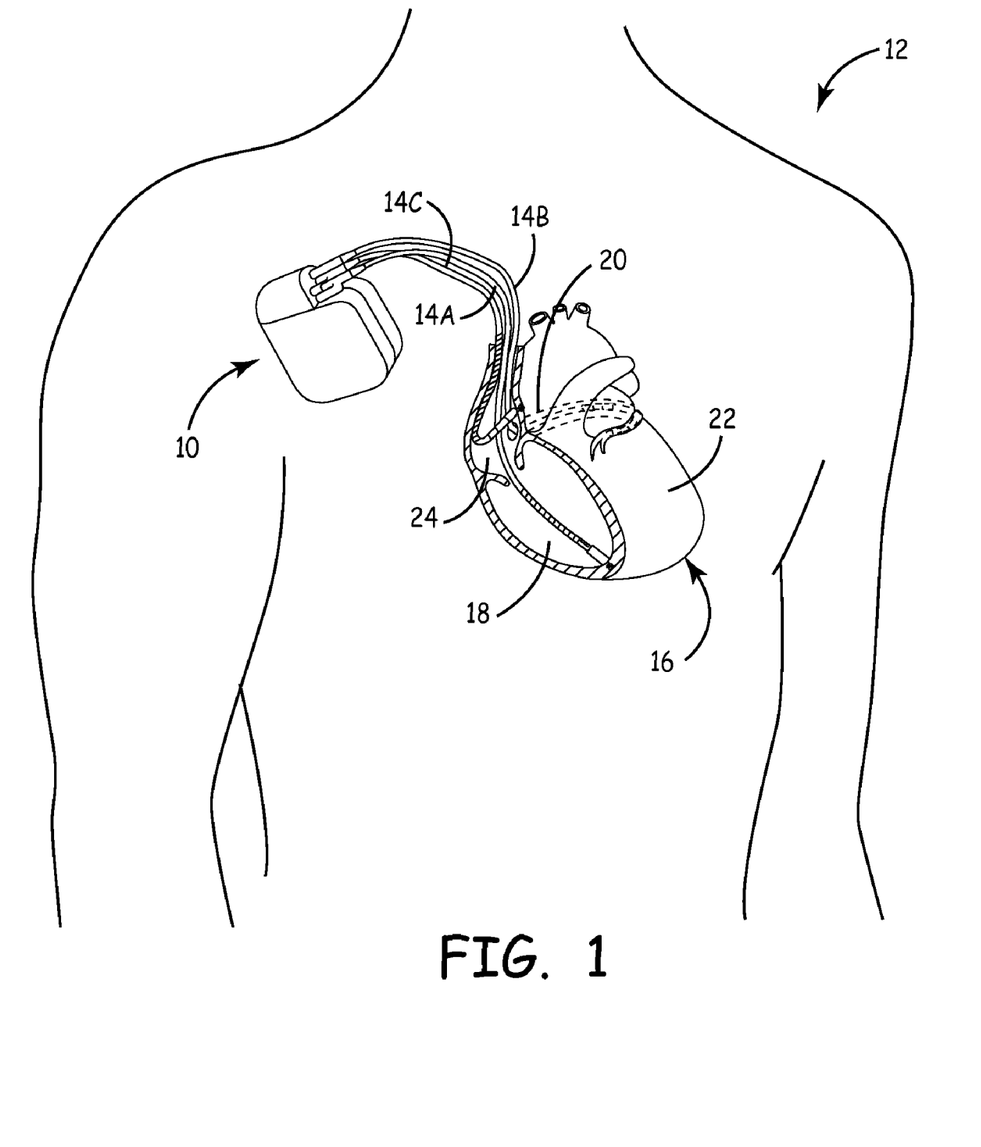
FIG. 1 is a conceptual diagram illustrating an implantable medical device (IMD) implanted in a patient.

FIG. 1 is a conceptual diagram illustrating an IMD 10 implanted in a patient 12. IMD 10 may take the form of a multi-chamber cardiac pacemaker as shown in FIG. 1. In the embodiment illustrated, IMD 10 is coupled to leads 14A, 14B and 14C (collectively "leads 14") that extend into the heart 16 of patient 12.

More particularly, right ventricular (RV) lead 14A may extend through one or more veins (not shown), the superior vena cava (not shown), and right atrium 24, and into right ventricle 18. Left ventricular (LV) coronary sinus lead 14B may extend through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

Each of leads 14 includes electrodes (not shown), which IMD 10 may use to sense electrical signals attendant to the depolarization and repolarization of heart 16, and to provide pacing pulses to heart 16. In some embodiments, IMD 10 may also provide cardioversion or defibrillation pulses via electrodes located on leads 14. The electrodes located on leads 14 may be selected in unipolar or bipolar sensing/stimulation configurations.

IMD 10 delivers cardiac resynchronization therapy to patient 12 via leads 14. In particular, as will be described in greater detail below, IMD 10 delivers pacing pulses to right ventricle 18 via lead 14A to synchronize contractions of right ventricle 18 with contractions of left ventricle 22 resulting from intrinsic depolarizations of left ventricle 22. One situation in which IMD 10 may be used is where patient 12 has right bundle branch block (RBBB), but has adequate physiological atrial-left ventricular conduction. By synchronizing contraction of ventricles 18 and 22 through pacing of right ventricle 22 alone, IMD 10 may provide a more physiological interval between atrial and ventricular contractions in the sense that the interval between the atrial and ventricular contractions is a function of an intrinsic, rather than paced, depolarization of the left ventricle with the right ventricular contraction synchronized to the left ventricular contraction. In addition, by pacing right ventricle 18 alone, IMD 10 may consume less power than conventional devices that provide cardiac resynchronization therapy by delivering pacing pulses to both the right ventricle 18 and left ventricle 22.

In various embodiments, IMD 10 determines the timing of delivery of pacing pulses to right ventricle 18 based on one or more measured cardiac event intervals corresponding to the sequence of electrical and/or mechanical events in the cardiac cycle and/or characteristics of an electrogram signal detected via one or more of leads 14 that represents electrical activity within heart 16. The measured intervals indicate a change in the normal temporal relation of cardiac cycle events due to the presence of RBBB. For example, in a normal patient, the first heart sound, corresponding to the closure of the atrioventricular valves and the onset of ventricular systole, occurs shortly after right ventricular depolarization. In a patient having RBBB, right ventricular depolarization is delayed resulting in the first heart sound (caused by left ventricular contraction) occurring before the right ventricular depolarization. By controlling the timing of delivery of right ventricular pacing pulses, the normal temporal relation of the right ventricular depolarization to the occurrence of the first heart sound can be restored, thereby improving ventricular synchrony.

The measured EGM characteristics can be used as metrics of synchrony between contractions of ventricles 18 and 22.

For example, wider QRS complex width indicates less synchronous contraction of ventricles 18 and 22. As another example, short Q-T intervals indicate increased sympathetic drive resulting from inadequate cardiac output, which in turn indicates dysynchrony of contraction of ventricles 18 and 22. Therefore, IMD 10 may, for example, select the right ventricular pace timing that results in the smallest QRS complex width, the largest Q-T interval, or the best combination of QRS complex width and Q-T interval.

The configuration of IMD 10 and leads 14 depicted in FIG. 1 is merely illustrative of one embodiment of the invention. IMD 10 may be coupled to any number of leads 14 that extend to a variety of positions within or outside of heart 16. For example, in some embodiments, IMD 10 may not be coupled to a left ventricular lead 14B. Further, lead 14C may extend to the left atrium of heart 16.

Some of leads 14 may be epicardial leads. Some electrodes used by IMD 10 to sense electrical activity of heart 16 need not be carried by leads 14 at all, but may instead be integral with a housing of IMD 10 (not shown), or carried by subcutaneous leads extending from IMD 10.

Figure 2:
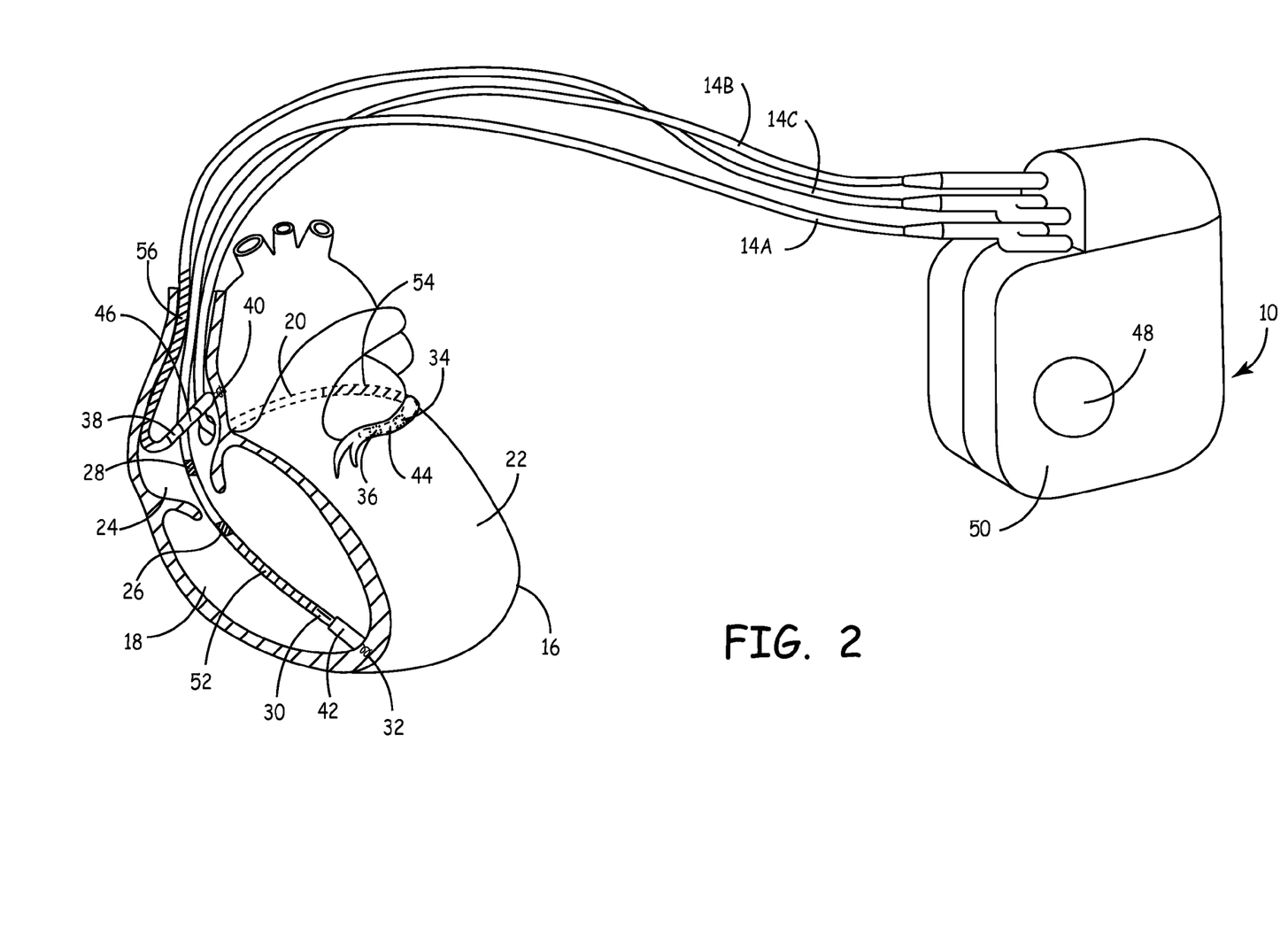
FIG. 2 is a conceptual diagram further illustrating the IMD of FIG. 1 and heart of a patient.

FIG. 2 is a conceptual diagram further illustrating IMD 10 and heart 16 of patient 12. Each of leads 14 may include an elongated insulative lead body carrying a number of insulated conductors (not shown). Located adjacent distal end of leads 14A, 14B and 14C are bipolar electrodes 30 and 32, 34 and 36, and 38 and 40 respectively. Electrodes 30, 34 and 38 may take the form of ring electrodes, and tip electrodes 32, 36 and 40 may take the form of extendable helix tip electrodes mounted retractably within insulative electrode heads 42, 44 and 46, respectively. Each of the electrodes 30-40 is coupled to one of the conductors within the lead body of its associated lead 14.

Sense/pace electrodes 30, 32, 34, 36, 38 and 40 sense electrical signals attendant to the depolarization and repolarization of heart 16. The electrical signals are conducted to IMD 10 via leads 14. Sense/pace electrodes 30, 32, 34, 36, 38 and 40 may deliver pacing to cause depolarization of cardiac tissue in the vicinity thereof. IMD 10 may also include one or more indifferent housing electrodes, such as housing electrode 48, formed integral with an outer surface of the hermetically sealed housing 50 of IMD 10. Any of electrodes 30, 32, 34, 36, 38 and 40 may be used for unipolar sensing or pacing in combination with housing electrode 48.

Leads 14A, 14B and 14C may also, as shown in FIG. 2, include elongated coil electrodes 52, 54 and 56, respectively. IMD 10 may deliver defibrillation or cardioversion shocks to heart 16 via coil electrodes 52-56. Coil electrodes 52-56 may be fabricated from platinum, platinum alloy or other materials known to be usable in implantable defibrillation electrodes, and may be about 5 cm in length.

Leads 14 further include sensors of mechanical physiological signals for use in measuring cardiac event intervals corresponding to the sequence of electrical and/or mechanical events in the cardiac cycle. In one embodiment, right ventricular lead 14A includes a sensor 28 for generating a signal responsive to heart sounds. Heart sound sensor 28 may be embodied as an accelerometer or other acoustical sensor adapted for use in an implantable medical device system. Sensors configured for sensing heart sounds are generally disclosed in U.S. Pat. No. 5,554,177 (Kieval, et al.) and U.S. Pat. No. 6,869,404 (Schulhauser et al.), both of which patents are hereby incorporated herein by reference in their entirety. As will be further described herein, heart sound sensor 28 can be used to detect the first heart sound for measuring an interval between an intrinsic right ventricular depolarization and the first heart sound. IMD 10 may then adjust a pacing interval for pacing the right ventricle 18 to improve the synchrony of the right ventricle 18 with the left ventricle 22 based on the measured interval. In alternative embodiments, heart sound sensor 28 may be positioned anywhere along any of leads 14 or along IMD housing 50.

Right ventricular lead 14A is further shown to include a pressure sensor 26 for use in sensing blood pressure signals in the right ventricle 18. In some embodiments of the invention, a pressure signal may be used in selecting a pacing interval for delivering right ventricular pacing pulses. Right ventricular dP/dtmax, dP/dtmin, end diastolic pressure, and an estimated pulmonary artery diastolic pressure are among the right ventricular pressure parameters that may be derived from a right ventricular pressure sensor signal. Such parameters may be used as a metric of ventricular synchrony assessed during selection of a pacing interval for pacing the right ventricle to improve synchrony between the paced right ventricular depolarization and the intrinsic left ventricular depolarization. A pressure sensor and methods for deriving right ventricular pressure parameters are generally disclosed in U.S. Pat. No. 5,368,040 (Carney), hereby incorporated herein by reference in its entirety.

Figure 3:
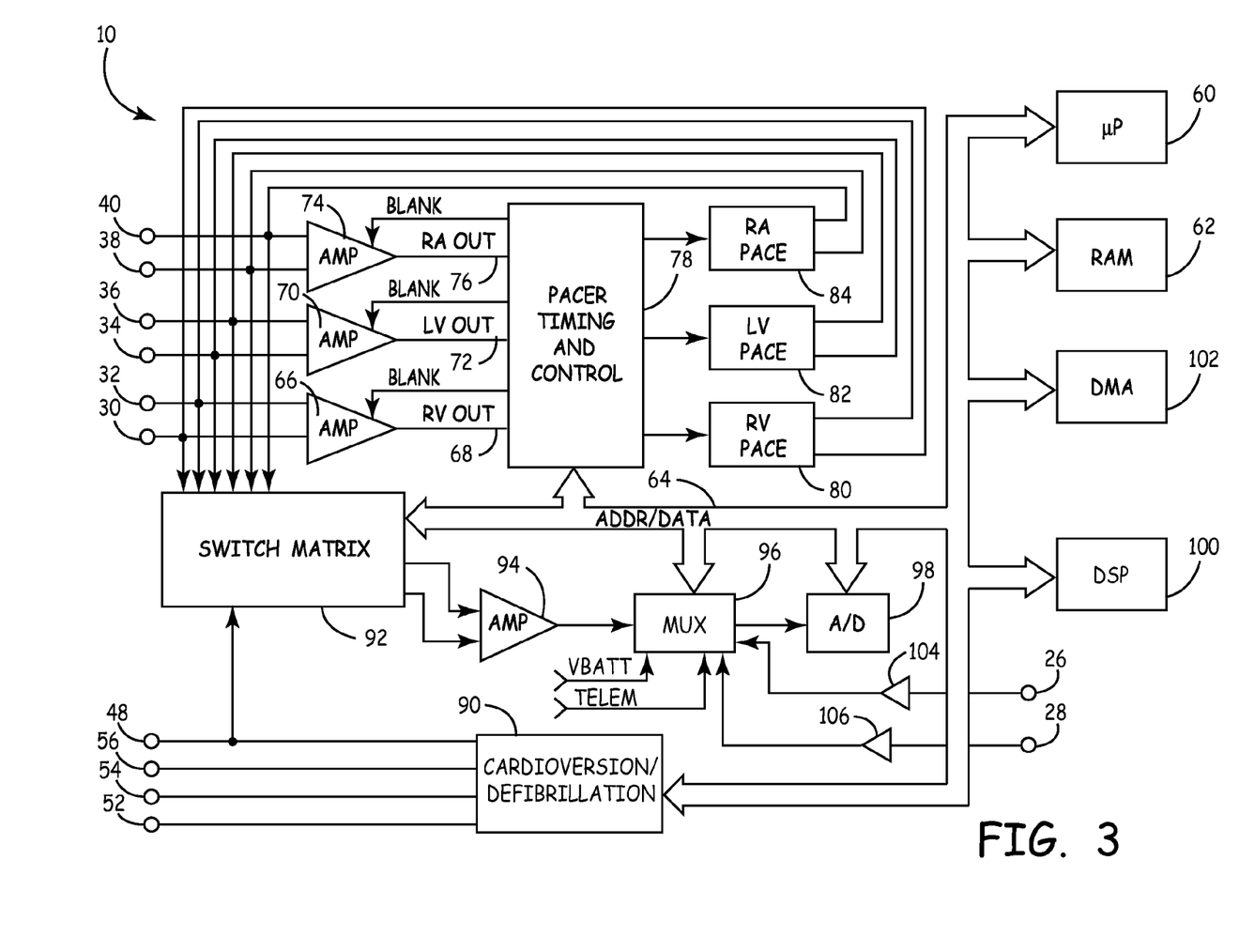
FIG. 3 is a functional block diagram of the IMD of FIG. 1.

FIG. 3 is a functional block diagram of IMD 10. As shown in FIG. 3, IMD 10 may take the form of a multi-chamber pacemaker-cardioverter-defibr-illator having a microprocessor-based architecture. However, this diagram should be taken as illustrative of the type of device in which various embodiments of the present invention may be embodied, and not as limiting, as it is believed that the invention may be practiced in a wide variety of device implementations, including devices that provide cardiac resynchronization pacing therapies but do not provide cardioverter and/or defibrillator functionality.

IMD 10 includes a microprocessor 60. Microprocessor 60 may execute program instructions stored in a memory, e.g., a computer-readable medium, such as a ROM (not shown), EEPROM (not shown), and/or RAM 62. Program instruction stored in a computer-readable medium and executed by microprocessor 60 control microprocessor 60 to perform the functions ascribed to microprocessor 60 herein. Microprocessor 60 may be coupled to, e.g., to communicate with and/or control, various other components of IMD 10 via an address/data bus 64.

IMD 10 senses electrical activity within heart 16. Electrodes 30 and 32 are coupled to amplifier 66, which may take the form of an automatic gain controlled amplifier providing an adjustable sensing threshold as a function of the measured R-wave amplitude. A signal is generated on RV out line 68 whenever the signal sensed between electrodes 30 and 32 exceeds the present sensing threshold. Thus electrodes 30 and 32 and amplifier 66 may be used to detect intrinsic right ventricular depolarizations.

Electrodes 34 and 36 are coupled to amplifier 70, which also may take the form of an automatic gain controlled amplifier providing an adjustable sensing threshold as a function of measured R-wave amplitude. A signal is generated on LV out line 72 whenever the signal sensed between electrodes 34 and 36 exceeds the present sensing threshold. Thus, electrodes 34 and 36 and amplifier 70 may be used to detect intrinsic left ventricular depolarizations.

Electrodes 38 and 40 are coupled to amplifier 74, which may take the form of an automatic gain controlled amplifier providing an adjustable sensing threshold as a function of the measured P-wave amplitude. A signal is generated on RA out line 76 whenever the signal between electrodes 38 and 40 exceeds the present sensing threshold. Thus, electrodes 38 and 40 and amplifier 74 may be used to detect intrinsic atrial depolarizations.

IMD 10 paces heart 16. Pacer timing/control circuitry 78 preferably includes programmable digital counters which control the basic time intervals associated with modes of pacing. Circuitry 78 also preferably controls escape intervals associated with pacing. For example, IMD 10 may pace right atrium 24 via timing/control circuitry 78 triggering generation of pacing pulses by pacer output circuit 84, which is coupled to electrodes 38 and 40. Pacer timing/control circuitry 78 may trigger generation of pacing pulses for right atrium 24 upon expiration of an atrial escape interval.

As mentioned above, IMD 10 delivers pacing pulses to right ventricle 18 to synchronize contractions of right ventricle 18 with contractions of left ventricle 22 resulting from intrinsic depolarizations of left ventricle 22. Pacer timing/control circuitry 78 triggers generation of pacing pulses for right ventricle 18 by pacer output circuit 80, which is coupled to electrodes 30 and 32. As will be described in greater detail below, circuitry 78 triggers generation of pacing pulses delivered to right ventricle 18 upon expiration of an interval that may be timed from a right atrial pacing pulse or detection of an intrinsic right atrial depolarization.

IMD 10 may also provide biventricular modes of cardiac resynchronization therapy, or non-resynchronization pacing modalities that require delivery of pacing pulses to left ventricle 22, and may switch from a right ventricular cardiac resynchronization mode as described herein to one of these additional modes. Pacer timing/control circuitry 78 triggers generation of pacing pulses for left ventricle 22 by pacer output circuit 82, which is coupled to electrodes 34 and 36. Pacer timing/control circuitry 78 may trigger generation of pacing pulses for left ventricle 22 upon expiration of an A-V or V-V escape interval, depending on the pacing mode.

Output circuits 80, 82 and 84 may be pulse generation circuits, which include capacitors and switches for the storage and delivery of energy as a pulse. Pacer timing/control circuitry 78 resets escape interval counters upon detection of R-waves or P-waves, or generation of pacing pulses, and thereby controls the basic timing of cardiac pacing functions. Intervals defined by pacing circuitry 78 may also include refractory periods during which sensed R-waves and P-waves are ineffective to restart timing of escape intervals, and the pulse widths of the pacing pulses. The durations of these intervals are determined by microprocessor 60 in response to data stored in RAM 62, and are communicated to circuitry 78 via address/data bus 64. Pacer timing/control circuitry 78 also determines the amplitude of the cardiac pacing pulses under control of microprocessor 60.

Microprocessor 60 may operate as an interrupt driven device, and is responsive to interrupts from pacer timing/control circuitry 78 corresponding to the occurrence of sensed P-waves and R-waves and corresponding to the generation of cardiac pacing pulses. Those interrupts are provided via data/address bus 64. Any necessary mathematical calculations to be performed by microprocessor 60 and any updating of the values or intervals controlled by pacer timing/control circuitry 78 take place following such interrupts.

Microprocessor 60 determines the timing of delivery of pacing pulses to right ventricle 18, i.e., the intervals provided to pacer timing/control circuit 78 to trigger generation of pacing pulses by output circuit 80, based on one or more measured cardiac event intervals corresponding to the sequence of electrical and/or mechanical events, e.g., an interval relating to the first heart sound, and/or measured EGM characteristics, e.g., QRS complex width or Q-T interval, of one or more electrogram signals that represent electrical activity within heart 16. IMD 10 receives signals that represent electrical activity within heart 16, and may digitally process the signals to measure characteristics of the signals. Switch matrix 92 is used to select which of the available electrodes 30-40 and 48 are coupled to wide band (0.5-200 Hz) amplifier 94 for use in digital signal analysis. As will be described in greater detail below, any of a number of potential combinations of these electrodes may be used, so long as the signal provided by the combination allows for identification and measurement of the desired characteristic. Selection of electrodes is controlled by microprocessor 60 via data/address bus 64, and the selections may be varied as desired.

The analog signals derived from the selected electrodes and amplified by amplifier 94 are provided to multiplexer 96, and thereafter converted to a multi-bit digital signal by A/D converter 98. A digital signal processor (DSP) 100 may process the multi-bit digital signals to measure QRS complex widths and/or Q-T intervals, as will be described in greater detail below. In some embodiments, the digital signal may be stored in RAM 62 under control of direct memory access circuit 102 for later analysis by DSP 100.

Analog signals received from right ventricular pressure sensor 26 and heart sound sensor 28 are amplified by amplifiers 104 and 106, respectively, and provided to multiplexer 96. The analog sensor signals are thereafter converted to digital signals by A/D converter 98. DSP 100 or microprocessor 60 receives the digital signals via address/data bus 64. The digital pressure signals are processed by DSP or microprocessor 60 to derive one or more right ventricular pressure parameters. The digital heart sound signal is processed by DSP 100 or microprocessor 60 for detecting heart sounds and deriving interval measurements relating to, in particular, the first heart sound. In alternative embodiments, analog circuitry may be used to detect the first heart sound using the analog heart sound sensor signal.

Although IMD 10 is described herein as having separate processors, microprocessor 60 may perform both the functions ascribed to it herein and digital signal analysis functions ascribed to DSP 100 herein. Moreover, although described herein in the context of microprocessor-based embodiment IMD 10, the invention may be embodied in various implantable medical devices that include one or more processors, which may be microprocessors, DSPs, FPGAs, or other digital logic circuits. Further, in some embodiments, IMD 10 may not include or utilize DSP 100 to measure QRS complex widths and Q-T intervals. For example, IMD 10 may include analog slope or threshold detecting amplifier circuits to identify the beginning and end points of QRS complexes or Q-waves and T-waves. In such embodiments of IMD 10, pacer timing/control circuit 78 may receive the output of these amplifier circuits, and provide an indication of the occurrence of these events to microprocessor 60 so that microprocessor may measure QRS complex widths and/or Q-T intervals. Likewise, peak detection, slope or threshold detecting amplifier circuits may be used for detecting and deriving right ventricular pressure parameters and the occurrence of the first heart sound.

IMD 10 may detect ventricular and/or atrial tachycardias or fibrillations of heart 16 using tachycardia and fibrillation detection techniques and algorithms known in the art. For example, the presence of a ventricular or atrial tachycardia or fibrillation may be confirmed by detecting a sustained series of short R-R or P-P intervals of an average rate indicative of tachycardia, or an unbroken series of short R-R or P-P intervals. IMD 10 is also capable of delivering one or more antitachycardia pacing (ATP) therapies to heart 16, and cardioversion and/or defibrillation pulses to heart 16 via one or more of electrodes 48, 52, 54 and 56.

Electrodes 48, 52, 54 and 56, are coupled to a cardioversion/defibrillation circuit 90, which delivers cardioversion and defibrillation pulses under the control of microprocessor 60. Circuit 90 may include energy storage circuits such as capacitors, switches for coupling the storage circuits to electrodes 48, 52, 54 and 56, and logic for controlling the coupling of the storage circuits to the electrodes to create pulses with desired polarities and shapes. Microprocessor 60 may employ an escape interval counter to control timing of such cardioversion and defibrillation pulses, as well as associated refractory periods.

Figure 4:
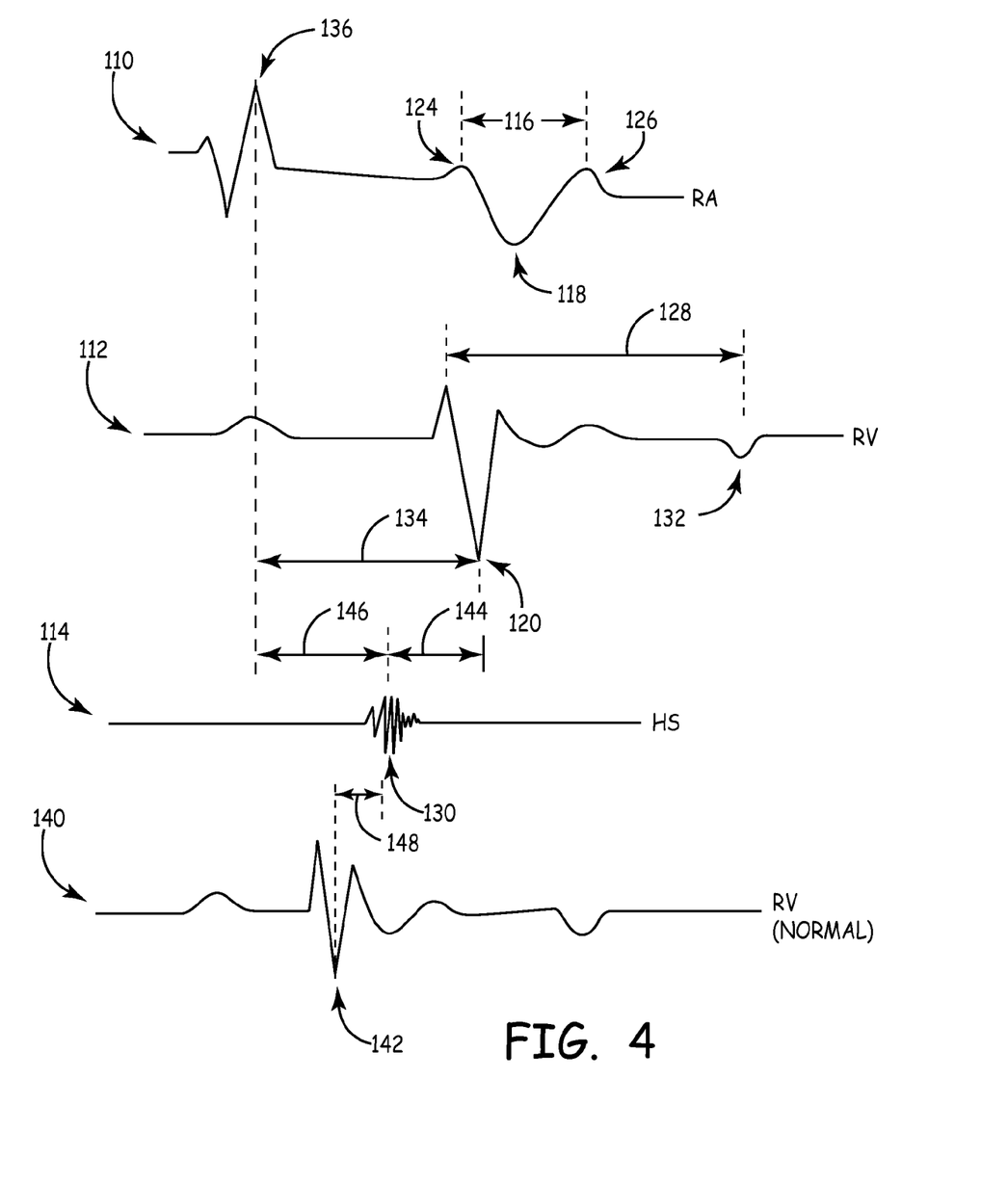
FIG. 4 is a timing diagram illustrating example electrogram (EGM) signals and heart sound signals that represent electrical and mechanical activity within a patient's heart.

FIG. 4 is a timing diagram illustrating example electrogram (EGM) signals and heart sound signals that represent electrical and mechanical activity within heart 16. Signal 110 is a right atrial EGM. IMD 10 may digitally process atrial EGM 110 to measure a width 116 of QRS complex 118. Signal 110 may be detected using electrodes 38 and 40 of RA lead 14C in a bipolar configuration, or one of electrodes 38 and 40 and housing electrode 48 in a unipolar configuration.

In general, IMD 10 digitally processes signals that include far-field QRS complexes 118, such as right atrial EGM 110, to measure widths 116. Processing these far-field signals results in QRS complex measurements that are more "global" in that they reflect depolarization of both ventricles 18, 22, and thus the widths 116 of far-field QRS complexes 118 more accurately reflect ventricular synchrony. In addition to atrial EGM signal 110, IMD 10 may detect signals that include far-field QRS complexes using two or more housing electrodes 48.

In order to measure QRS complex width 116, DSP 100 first identifies far-field QRS complex 118 within signal 110. For example, DSP 100 may receive indications of the occurrence of an R-wave 120 or 122 from pacer timing/control circuit 78, and identify QRS complex 118 based on these indications. As another example, DSP 100 may identify QRS complex 118 by detecting a number of threshold-crossings of the digital signal provided by A/D converter 98, or zero-crossings of the first derivative of the digital signal occurring within a time window. As yet another example, DSP 100 may detect QRS complexes within signals 110, 112 using techniques described in commonly assigned U.S. Pat. No. 6,029,087 (Wohlgemuth), hereby incorporated herein by reference in its entirety.

DSP 100 may measure width 116 as a period of time from a beginning point 124 to an ending point 126. DSP 100 may identify beginning point 124 and ending point 126 as threshold-crossings of the digital signal or zero-crossings of the first derivative of the digital signal.

Signal 112 is a right EGM and is detected via RV lead 14A. Signal 112 may be detected using bipolar electrode pair 30 and 32 or one electrode 30 or 32 and housing electrode 48 in a unipolar configuration. IMD 10 may digitally process signal 112 to measure a Q-T interval 128. For example, DSP 100 may receive an indication of delivery of a right ventricular pacing pulse (not shown) from pacer timing/control circuitry 78, and measure Q-T interval 128 as the period of time from the pacing pulse to detection of T-wave 132 within the digital signal provided by A/D converter 98. T-wave 132 may, for example, be detected using techniques described in the above-referenced Wohlgemuth '087 patent.

For ease of illustration, only a portion of each of EGM signals 110, 112 representing a single cardiac cycle of heart 16 is shown in FIG. 4. However, it is understood that DSP 100 may measure multiple QRS complex widths and/or Q-T intervals over multiple cardiac cycles. As will be described in greater detail below, DSP 100 measures these values in response to delivery of pacing pulses to right ventricle 18. The values for QRS complex widths 116 and/or Q-T intervals 128 measured by DSP 100 may be stored in RAM 62 for later analysis by microprocessor 60. Microprocessor 60 analyzes the measured values to identify the smallest QRS complex width 116 or the largest Q-T interval 128 in response to a range or test right atrial-ventricular (AV) pacing intervals.

In various embodiments of IMD 10, microprocessor 60 may measure intervals 134 between intrinsic and/or paced atrial depolarizations, e.g., P-waves 136, and intrinsic right ventricular depolarizations, e.g., R-waves 120. Microprocessor 60 controls pacer timing/control circuitry 78 to deliver test right ventricular pacing pulses (not shown) at a variety of pacing intervals timed from P-wave 136. Microprocessor 60 may control circuit 78 to test pacing intervals within a range defined based on interval 134, for example test AV pacing intervals less than interval 134.

In some embodiments, DSP 100 measures one or both of a QRS complex width 116 and Q-T interval 128 for each pacing interval tested. Microprocessor 60 selects the tested pacing interval that microprocessor 60 determines provides the best synchronization between contractions of right and left ventricles 18 and 22, e.g., the pacing interval that resulted in the shortest QRS complex width 116, the longest Q-T interval 128, or the average of the pacing intervals that resulted in the shortest QRS complex width 116 and the longest Q-T interval 128, respectively. Microprocessor 60 then controls delivery of pacing pulses to right ventricle 18 based on the selected pacing interval, as will be described in greater detail below.

Signal 114 illustrates a first heart sound (FHS) signal obtained from heart sound sensor 28. The R-wave 120 occurs at an interval 144 after the FHS 130 in patients having RBBB. Signal 140 illustrates a right ventricular EGM signal obtained from a healthy patient having intact atrial-ventricular conduction. R-wave 142 occurs prior to FHS 130, by an interval 148, corresponding to normal ventricular synchrony. In some embodiments, the interval 144 between an intrinsic R-wave 120 sensed in a patient having RBBB and the FHS 130 is measured for use in determining a pacing interval for pacing the right ventricle 18 to improve synchrony between the right ventricle 18 and the left ventricle 22. Alternatively, the interval 146 measured between a P-wave 136 in the right atrium and the FHS 130 in a patient known to have RBBB may be used for selecting a pacing interval for pacing the right ventricle. For example, a pacing interval following P-wave 136 may be applied to deliver a pacing pulse prior to FHS 130 to thereby restore the normal temporal relationship between the right ventricular depolarization and FHS 130 as represented, for example, by signal 140.

FHS 130 may be sensed using a threshold crossing, slope detection, frequency threshold, or other signal processing methods for sensing FHS subsequent to the atrial P-wave 136 or an atrial pacing pulse. As will be further described herein, a range of test AV pacing intervals may be applied to select the AV pacing interval that results in the right ventricular depolarization occurring prior to the FHS by a desired interval corresponding to a normal temporal relationship as represented by signal 140. Alternatively, the interval 146 between P-wave 136 and FHS 130 may be set as a maximum right AV pacing interval used in selecting the right AV pacing interval based on other assessments of ventricular synchrony involving measured EGM characteristics and/or right ventricular pressure parameters.

Figure 5:
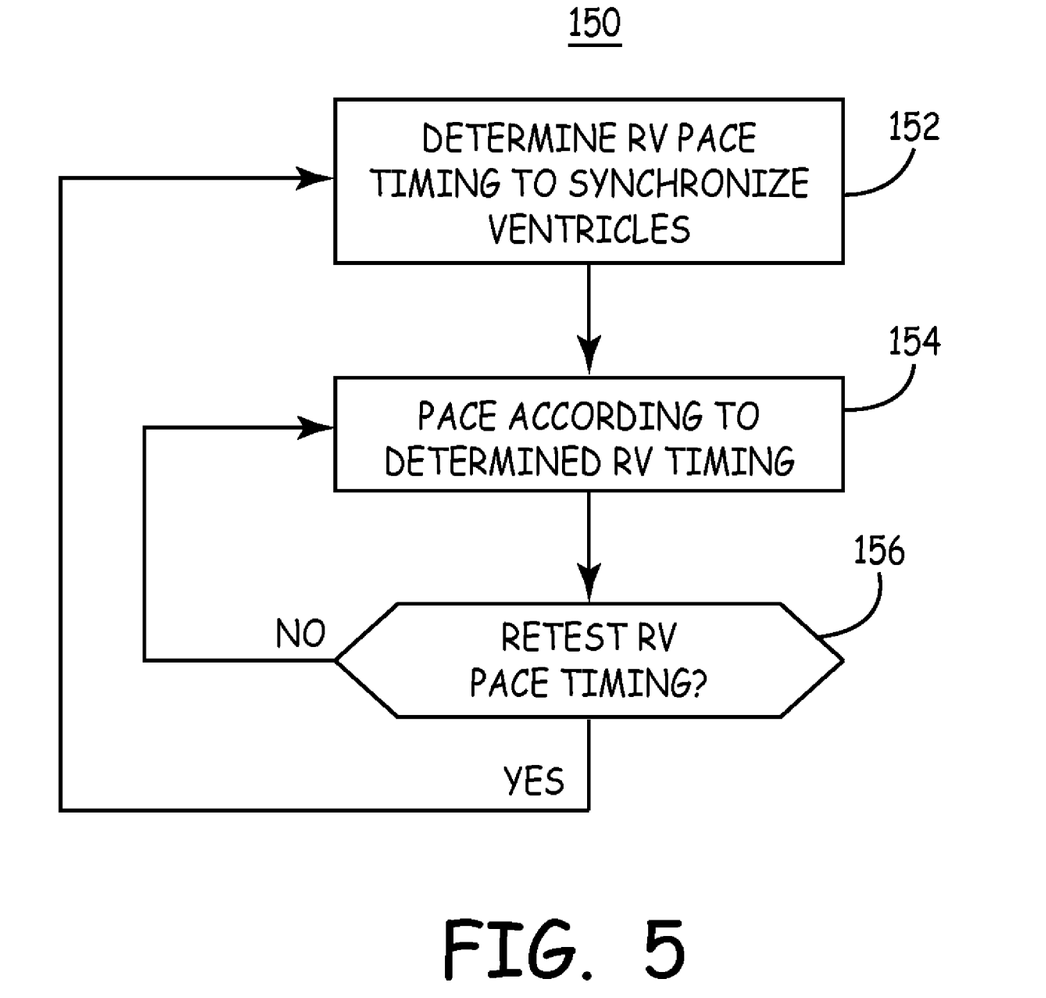
FIG. 5 is a flow diagram illustrating an example method that the IMD of FIG. 1 may employ to deliver cardiac resynchronization therapy according to one embodiment the invention.

FIG. 5 is a flow diagram illustrating an example method 150 that IMD 10 may employ to deliver cardiac resynchronization therapy according to one embodiment of the invention. Flow chart 150 is intended to illustrate the functional operation of IMD 10, and should not be construed as reflective of a specific form of software or hardware necessary to practice the invention. It is believed that the particular form of software will be determined primarily by the particular system architecture employed in the IMD and by the particular detection and therapy delivery methodologies employed by the IMD. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

In general, IMD 10, and more particularly microprocessor 60 of IMD 10, determines a timing of right ventricular pacing at block 152 that synchronizes the paced contractions of right ventricle 18 with contractions of left ventricle 22 resulting from intrinsic depolarizations of left ventricle 22. Processor 60 determines the timing of right ventricular pacing based on measured intervals using electrogram and other sensor signals, including a heart sound sensor. Processor 60 controls pacing of right ventricle 18 based on the determined timing at block 154. Processor 60 periodically retests the timing of right ventricular pacing, e.g., hourly, daily, or monthly, to account for longer-term changes in the condition of patient 12, as indicated by block 156. Method 150 and variations thereof as will be described below can be applied independently of the pacing/sensing sites for the right and left ventricles.

Figure 6:
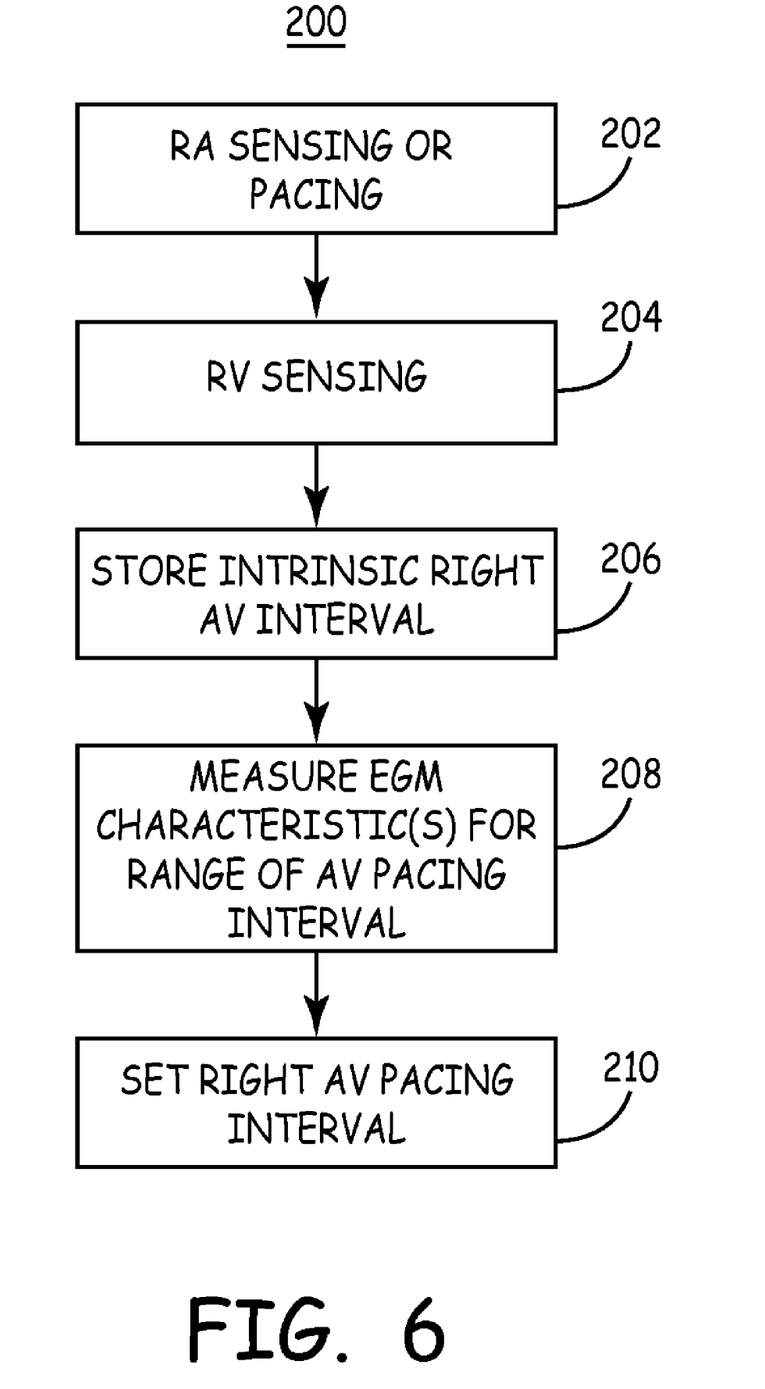
FIG. 6 illustrates a method that may be employed by the IMD of FIG. 1 to determine right ventricular pacing timing based on a measured EGM characteristic.

FIGS. 6-9 further illustrate A method according to FIG. 5 according to various embodiments of the invention. FIG. 6 illustrates a method 200 that may be employed by IMD 10 to determine the timing based on a measured EGM characteristic. At blocks 202 and 204, right atrial sensing and right ventricular sensing, respectively, are performed to detect the intrinsic right atrial depolarization (P-wave) and the intrinsic right ventricular depolarization (R-wave). The intrinsic right AV interval is measured based on the sensed depolarization signals, for example interval 134 shown in FIG. 4, at block 206. The measured intrinsic right AV interval is stored at block 206 and used in setting a range of test AV pacing intervals applied for pacing the right ventricle. In one embodiment, test AV pacing intervals are set to multiple settings between a minimum AV interval, for example 30 ms, and a maximum AV interval equal to the measured intrinsic right AV interval.

At block 208, EGM characteristics are measured during right ventricular pacing at each applied AV interval. The EGM characteristics measured may include the QRS duration (116 in FIG. 4) and/or the QT interval (128 in FIG. 4). At block 210 the right AV pacing interval for pacing the right ventricle 18 is set based on the measured EGM characteristics. In one embodiment, the AV pacing interval is set to the interval corresponding to the shortest QRS duration. In another embodiment the AV pacing interval is set to the interval corresponding to the longest QT interval. In yet another embodiment, the AV pacing interval is set to an interval determined as a function of both of the interval corresponding to the shortest QRS duration and the interval corresponding to the longest QT interval. For example, the AV pacing interval may be set as an average of these intervals.

As indicated at block 202, method 200 may be performed during both atrial sensing and atrial pacing. In other words, the interval measured at block 206 may be a right AV interval corresponding to a right atrial pace and the intrinsic right ventricular depolarization following the right atrial pace. A range of test AV pacing intervals may then be applied following the right atrial pace. The range of test AV pacing intervals can be defined based on the measured right atrial pace to intrinsic right ventricular depolarization interval. For example the measured right atrial pace to intrinsic right ventricular depolarization interval may be used as a maximum AV pacing interval. The EGM characteristics measured at block 208 are measured during right atrial and right ventricular pacing over the range of test AV pacing intervals. The right AV pacing interval set at block 210 based on EGM characteristics measured during right atrial pacing may be stored separately from the right AV pacing interval determined during right atrial sensing. Accordingly, a different right AV pacing interval for synchronizing the right ventricle 18 with the left ventricle 22 may be applied during right atrial pacing than during right atrial sensing.

Figure 7:
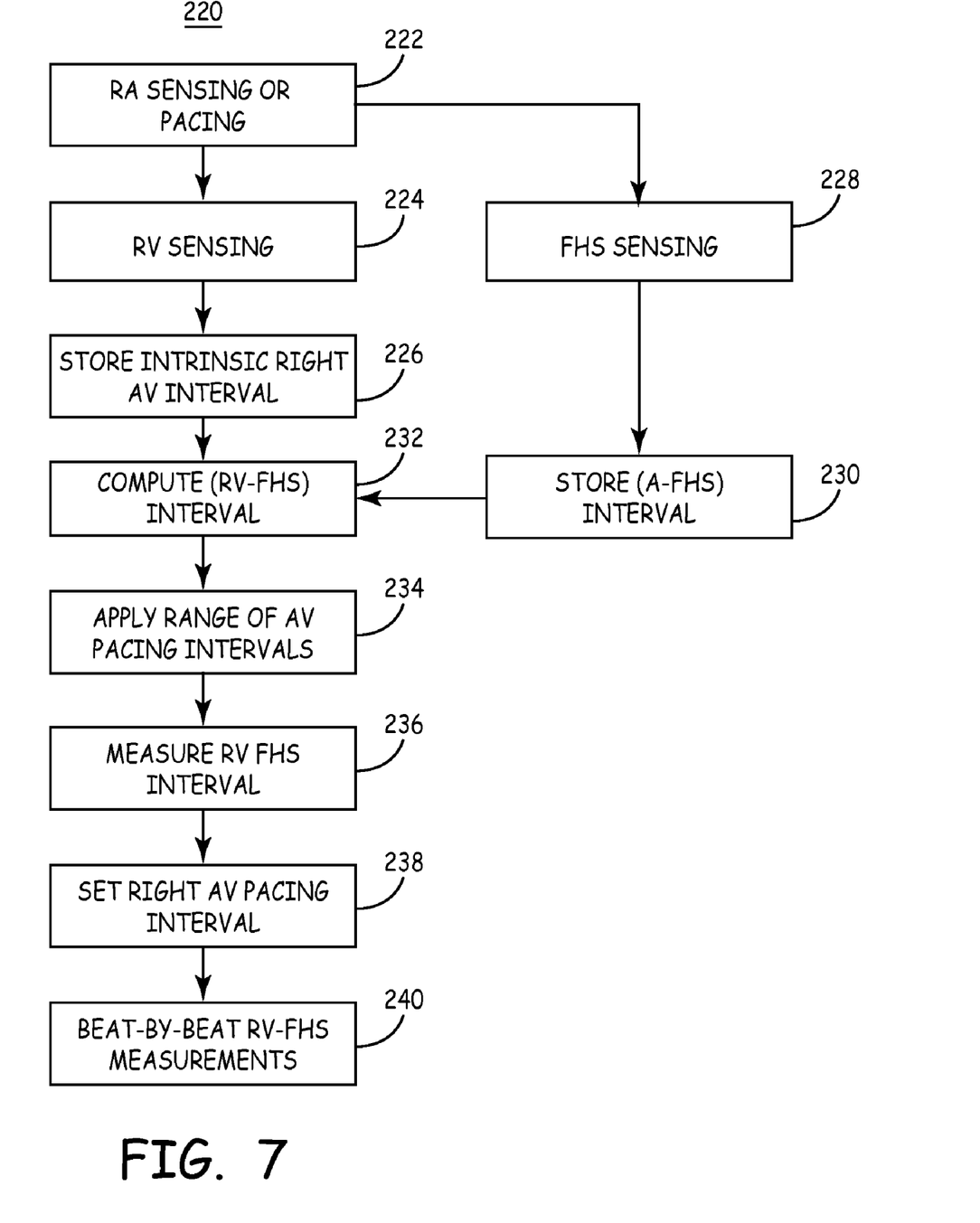
FIG. 7 is flow chart of a method that may be employed by the IMD of FIG. 1 to determine the right ventricular pacing timing based on a measured interval between cardiac cycle events.

FIG. 7 is flow chart of a method 220 that may be employed by IMD 10 to determine the right ventricular pacing timing based on a measured interval between cardiac cycle events. In particular, the right ventricular pacing timing is regulated relative to the FHS. At blocks 222 and 224, right atrial sensing and right ventricular sensing, respectively, are performed as described above for measuring an intrinsic right AV interval at block 226. Method 220 may additionally or alternatively be performed during right atrial pacing, as indicated at block 222, for measuring an interval between a right atrial pace and subsequent intrinsic right ventricular depolarization. In this case, method 220 is used to set an AV pacing interval to be applied to the right ventricle 18 during right atrial pacing for synchronizing the right and left ventricles 18 and 22.

At block 228, the heart sound sensor 28 is used to sense the occurrence of the first heart sound. An interval between the atrial sense/pace and the FHS (A-FHS interval) is measured at block 230. In some embodiments, this interval may be used for setting the right AV pacing interval to synchronize the RV depolarization relative to the FHS. For example, the A-FHS interval stored at block 230 less a predetermined offset may be set as the right AV pacing interval such that the right ventricle 18 is paced at the predetermined offset prior to the FHS. In one embodiment, the AV pacing interval is set as the A-FHS interval less an offset of about 10 to 200 ms.

At block 232, the difference between the intrinsic AV interval and the A-FHS interval is computed as the RV-FHS interval. This difference may be used to determine a right AV pacing interval that results in an improved temporal relation between the RV depolarization and the FHS in a patient having RBBB.

At block 234, a range of test AV pacing intervals is applied to pace the right ventricle 18. The range of test AV pacing intervals may be defined based on the measured intrinsic AV interval as described previously. Alternatively, the range of test AV pacing intervals may be defined based on the measured A-FHS interval, e.g. the maximum test AV pacing interval may equal to the A-FHS interval. At block 236 the RV-FHS interval is determined for each respective AV pacing interval. At block 238, the AV pacing interval that results in an RV-FHS interval that is considered to be physiologically acceptable, i.e., associated with improved RV-LV synchrony, is set as the right AV pacing interval. For example, the AV pacing interval that results in an RV-FHS interval of about 40 ms, i.e. the RV depolarization occurs about 40 ms prior to the FHS, is selected at block 238 as the right AV pacing interval.

At block 240, the RV-FHS interval may be measured on a beat-by-beat or other periodic basis for dynamically resetting the AV pacing interval to maintain ventricular synchrony. For example, the RV-FHS interval measurement performed on each cardiac cycle may be used to adjust the AV pacing interval on subsequent cardiac cycles. In one embodiment, a rolling average of the RV-FHS interval is determined for a predetermined number of cardiac cycles. If the rolling average begins to increase greater than the desired RV-FHS interval, the right AV pacing interval may be lengthened to pace the RV somewhat later in the cardiac cycle. If the rolling average begins to decrease, the right AV pacing interval may be shortened to pace the RV somewhat earlier in the cardiac cycle. Alternatively, if the rolling average or a consecutive number of RV-FHS intervals fall outside an acceptable RV-FHS interval range, the method 220 may return to block 234 to reassess a range of test AV pacing intervals and reset the right AV pacing interval at block 238 based on RV-FHS interval measurements.

Figure 8:
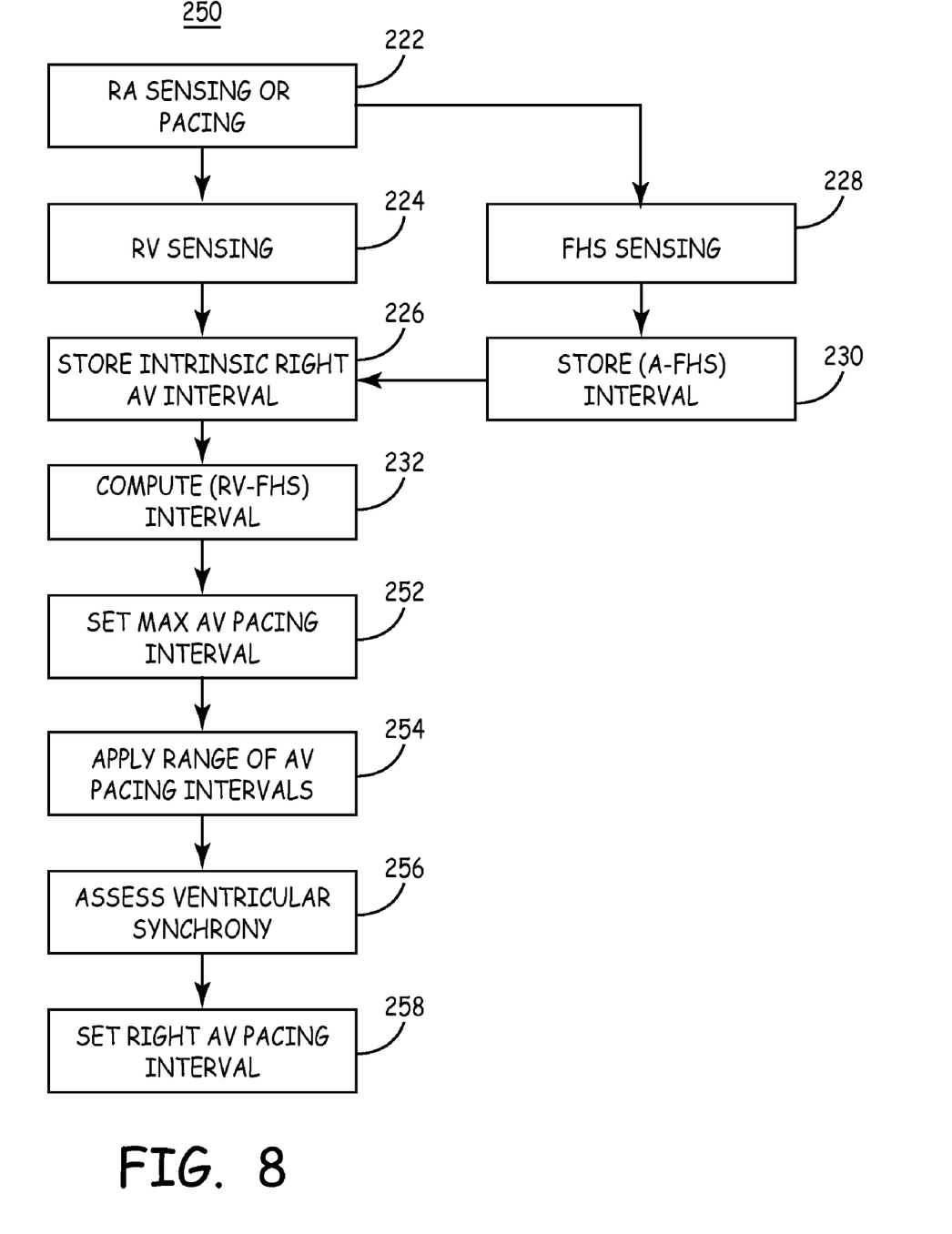
FIG. 8 is a flow chart of an alternative method for setting a right atrial-ventricular (AV) pacing interval for improving ventricular synchrony.

FIG. 8 is a flow chart of an alternative method 250 for setting a right AV pacing interval for improving RV-LV synchrony. In method 250, blocks 222 through 232 correspond to identically numbered blocks described in conjunction with method 220 of FIG. 7. At block 252, a maximum AV pacing interval may be defined based on the measured A-FHS interval (block 230). This maximum AV pacing interval prevents the pacing interval to be set based on other parameter assessment to an interval that results in RV pacing after the FHS.

At block 254, a range of test AV pacing intervals are applied, which may be set between a minimum and the maximum AV pacing interval set at block 252. At block 256, ventricular synchrony is assessed by measuring one or more ventricular synchrony metrics for each respective test AV pacing interval. EGM characteristics, such as QRS width and QT interval may be measured to assess ventricular synchrony at block 256. Additionally or alternatively, a right ventricular pressure parameter, as derived from an RV pressure sensor signal, may be determined as a ventricular synchrony metric. RV pressure parameters may include dP/dtmax, dP/dtmin, end diastolic pressure, and an estimated pulmonary artery diastolic pressure.

At block 258, the right AV pacing interval is set as a function of the AV pacing intervals corresponding to the optimal ventricular synchrony as indicated by the measured ventricular synchrony metrics. For example, the test AV pacing intervals corresponding to each of the minimum QRS duration, maximum QT interval, maximum RV dp/dt(max), minimum RV end diastolic pressure, and/or minimum estimated diastolic pulmonary artery pressure may be determined. The RV-FHS interval may additionally be measured for each AV pacing interval.

The right AV pacing interval may then be set at block 258 to an interval corresponding to any of these optimal ventricular synchrony metrics or as a function of any combination of these intervals. The right AV pacing interval is set to be equal to or less than the maximum interval determined at block 252 to maintain a normal temporal relationship between the RV depolarization and the FHS.

Figure 9:
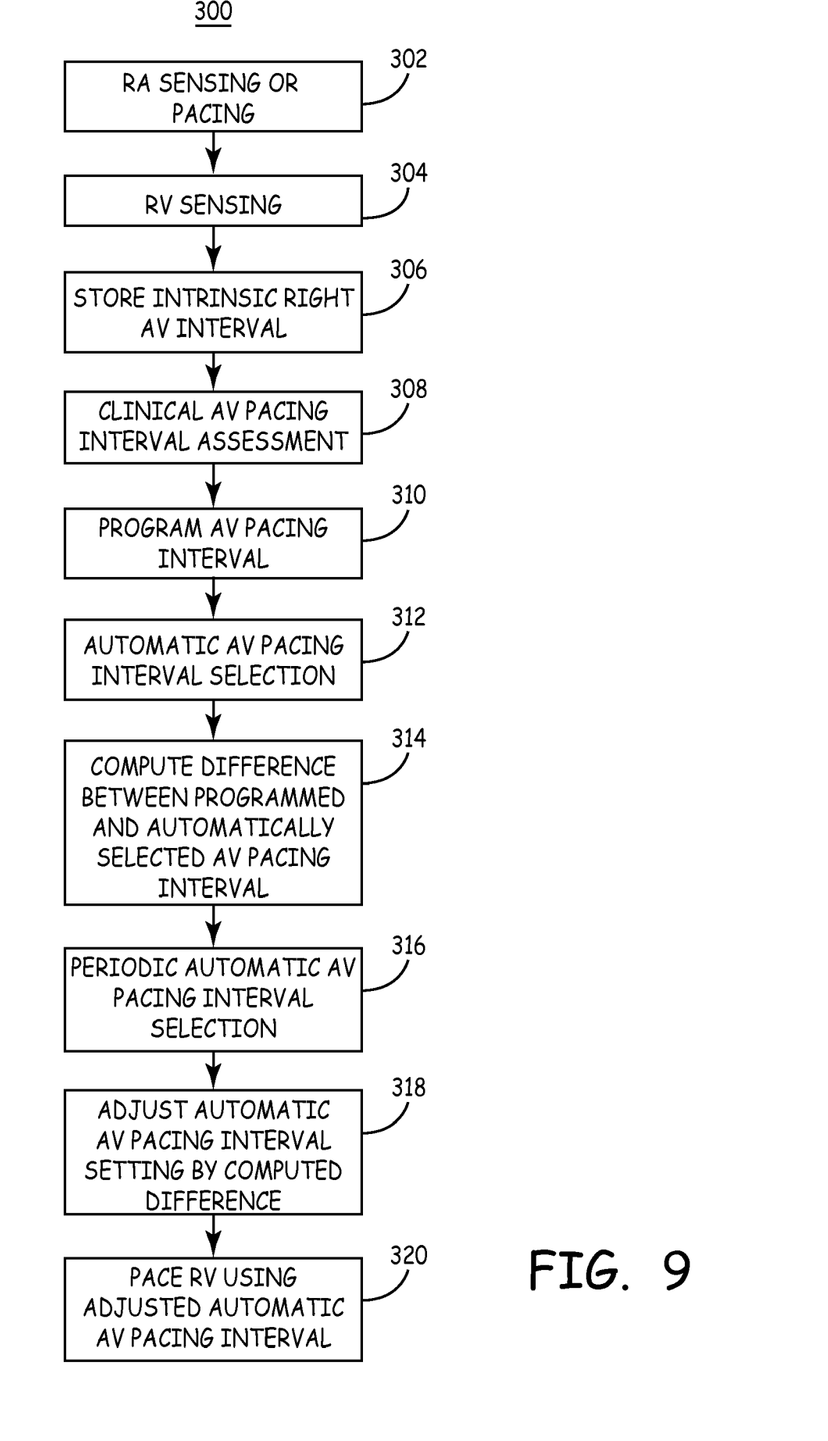
FIG. 9 is a flow chart of another method for controlling right ventricular pacing for improving synchrony of the right ventricle with intrinsic left ventricular depolarizations.

FIG. 9 is a flow chart of another method 300 for controlling RV pacing for improving synchrony of the RV with intrinsic LV depolarizations. At blocks 302 and 304 right atrial sensing/pacing and right ventricular sensing, respectively, are performed for measuring an intrinsic right AV interval at block 306. At block 308, a clinical assessment of RV-LV synchrony is performed while applying a range of AV pacing intervals. The range of AV pacing intervals may be selected based on the measured intrinsic right AV interval as described previously. The clinical assessment may include ECG analysis, echocardiogram analysis, heart sound analysis, fluoroscopy, or other clinical evaluation tools. At block 310, a right AV pacing interval determined to improve RV-LV synchrony based on the clinical assessment is programmed by a clinician.

At block 312, an automatic AV pacing interval selection is performed by IMD 10. The automatic AV pacing interval selection method may correspond to any of the methods shown in FIGS. 6-8 or any combination of these methods. The automatic AV pacing interval selection may include determining the timing of the right ventricular depolarization relative to the FHS as well as determining other ventricular synchrony metrics, such as EGM characteristics and RV pressure parameters. The automatic selection method is performed to determine an AV pacing interval setting that optimally improves ventricular synchrony according to IMD-measured parameters. The automatically selected AV pacing interval is determined immediately after programming the AV pacing interval such that a difference between the programmed and automatically selected AV pacing interval may be determined. The difference between an AV pacing interval determined by the automatic selection method for optimally improving ventricular synchrony and the programmed AV pacing interval is computed at block 314.

The difference is not used to adjust the currently programmed AV pacing interval. Rather, this difference is stored for use in adjusting automatically selected AV pacing intervals upon subsequent AV pacing interval assessments. As such, following a periodic automatic AV pacing interval assessment performed at block 316, the AV pacing interval selected by the automatic selection method is adjusted by the difference computed at block 318 between the automatically selected AV pacing interval determined previously and a clinically determined AV pacing interval. The adjusted automatic AV pacing interval is used to pace the right ventricle at block 320.

Thus, a device and methods have been presented in the foregoing description for pacing a right ventricle in patients with RBBB for improving synchrony between the right ventricle and an intrinsically activated left ventricle with reference to specific embodiments. It is appreciated that various modifications to the referenced embodiments may be made without departing from the scope of the invention as set forth in the following claims.

The invention claimed is:

1. A method for use in an implantable medical device for delivering cardiac resynchronization therapy in a patient having right bundle branch block, comprising:
   measuring a first interval between a right atrial depolarization signal and a first heart sound signal;
   selecting a right atrial-ventricular (AV) pacing interval in response to the measured first interval; and
   delivering pacing pulses to a right ventricle of a heart at the selected right AV pacing interval; further comprising:
   measuring a second interval between the right atrial depolarization and a right ventricular depolarization;
   delivering pacing pulses to the right ventricle at a plurality of test AV pacing intervals determined based on the second interval; and
   assessing ventricular synchrony by determining a metric of ventricular synchrony for each of the plurality of test AV pacing intervals;
   wherein selecting the right AV pacing interval further comprises determining an optimal right AV pacing interval by comparing the metric of ventricular synchrony for each of the plurality of test AV pacing intervals.

2. A method according to claim 1 wherein assessing ventricular synchrony comprises computing a third interval between the right ventricular depolarization and the first heart sound for each of the plurality of test AV pacing intervals.

3. A method according to claim 1 wherein assessing ventricular synchrony comprises measuring a cardiac electrogram characteristic for each of the plurality of test AV pacing intervals.

4. A method according to claim 3 wherein the cardiac electrogram characteristic is one of a QRS duration and a QT interval.

5. A method according to claim 1 wherein assessing ventricular synchrony comprises measuring a right ventricular pressure parameter for each of the plurality of test AV pacing intervals.

6. A method according to claim 5 wherein the right ventricular pressure parameter is one of a maximum dP/dt, an end diastolic pressure, and an estimated pulmonary artery pressure.

7. An implantable medical device to provide cardiac resynchronization therapy in a patient having right bundle branch block, the device comprising:
    electrodes to detect electrical signals within a heart and deliver pacing pulses to the heart;
    sensing circuitry for receiving the electrical signals from the electrodes;
    pulse generating circuitry for generating the pacing pulses delivered by the electrodes;
    a heart sound sensor; and
    a processor coupled to the sensing circuitry, the pulse generating circuitry, and the heart sound sensor and configured to measure a first interval between a right atrial depolarization signal and a first heart sound signal, select a right atrial-ventricular (AV) pacing interval in response to the measured first interval; and control the delivery of pacing pulses to a right ventricle of a heart at the selected right AV pacing interval, wherein the processor is further configured to:
    measure a second interval between the right atrial depolarization signal and a sensed right ventricular depolarization signal;
    control the delivery of pacing pulses to the right ventricle at a plurality of test AV pacing intervals determined based on the second interval; and
    perform an assessment of ventricular synchrony by determining a metric of ventricular synchrony for each of the plurality of test AV pacing intervals;
    wherein selecting the right AV pacing interval by the processor comprises comparing the metric of ventricular synchrony for each of the plurality of test AV pacing intervals.

8. A device according to claim 7 wherein the assessment of ventricular synchrony performed by the processor comprises computing a third interval between the right ventricular depolarization and the first heart sound for each of the plurality of test AV pacing intervals.

9. A device according to claim 7 wherein the assessment of ventricular synchrony performed by the processor comprises measuring a cardiac electrogram characteristic for each of the plurality of test AV pacing intervals.

10. A device according to claim 7 wherein the assessment of ventricular synchrony performed by the processor comprises measuring a right ventricular pressure parameter for each of the plurality of test AV pacing intervals.

11. A device according to claim 7 wherein the processor being further configured to:
    determine a difference between the selected right AV pacing interval and a programmed interval,
    adjust the selected AV pacing interval by the difference,
    repeat the ventricular synchrony assessment to determine a next selected right AV pacing interval; and
    adjust the next selected AV pacing interval by the difference.

12. A non-transitory computer-readable medium for storing a set of instructions which when implemented in an implantable medical device for delivering cardiac resynchronization therapy causes the device to:
    measure a first interval between a right atrial depolarization signal and a first heart sound signal;
    select a right atrial-ventricular (AV) pacing interval in response to the measured first interval;
    deliver pacing pulses to a right ventricle of a heart at the right AV pacing interval:
    measure a second interval between the right atrial depolarization and a right ventricular depolarization;
    deliver pacing pulses to the right ventricle at a plurality of test AV pacing intervals determined based on the second interval; and
    assess ventricular synchrony by determining a metric of ventricular synchrony for each of the plurality of test AV pacing intervals;
    wherein selecting the right AV pacing interval further comprises determining an optimal right AV pacing interval by comparing the metric of ventricular synchrony for each of the plurality of test AV pacing intervals.

* * * * *